United States Patent
Nace et al.

(10) Patent No.: US 9,265,646 B2
(45) Date of Patent: Feb. 23, 2016

(54) ORTHOTIC DEVICE FOR TREATING KNEE FLEXION CONTRACTURE

(71) Applicant: MEDICAL ALLIANCE S.A., San Jose (CR)

(72) Inventors: Richard A Nace, San Jose (CR); Anil Bhave, Timonium, MD (US)

(*) Notice: Subject to any disclaimer, the term of this patent is extended or adjusted under 35 U.S.C. 154(b) by 353 days.

(21) Appl. No.: 13/864,310

(22) Filed: Apr. 17, 2013

(65) Prior Publication Data

US 2014/0316317 A1 Oct. 23, 2014

(51) Int. Cl.
*A61F 5/00* (2006.01)
*A61F 5/01* (2006.01)

(52) U.S. Cl.
CPC ....... *A61F 5/0125* (2013.01); *A61F 2005/0167* (2013.01); *A61F 2005/0172* (2013.01); *A61F 2005/0179* (2013.01)

(58) Field of Classification Search
CPC ... A61F 5/0111; A61F 5/0123; A61F 5/0125; A61F 5/05816; A61F 5/2585; A61F 2005/0167; A61F 2005/0172; A61F 2005/0179
USPC ............... 602/5, 13, 16, 23, 26–29; 128/882; D24/190–192
See application file for complete search history.

(56) References Cited

U.S. PATENT DOCUMENTS

| | | | | |
|---|---|---|---|---|
| 8,308,669 B2* | 11/2012 | Nace | ................ | A61F 5/0125 602/16 |
| 8,308,671 B2* | 11/2012 | Nace | ................ | A61F 5/0123 602/23 |
| 8,376,974 B2* | 2/2013 | Nace | ................ | A61F 5/0123 601/35 |
| 8,672,865 B2* | 3/2014 | Franke et al. | ................ | 602/23 |
| 8,945,035 B2* | 2/2015 | Nace | ................ | A61F 5/0123 602/23 |
| 2009/0292229 A1* | 11/2009 | Nace | ................ | 602/16 |
| 2010/0125231 A1* | 5/2010 | Knecht | ................ | 602/26 |
| 2010/0323859 A1* | 12/2010 | Von Hoffmann et al. | .... | 482/124 |
| 2011/0105969 A1* | 5/2011 | Nace | ................ | 602/16 |
| 2011/0152736 A1* | 6/2011 | Ng | ................ | 602/16 |
| 2011/0282255 A1* | 11/2011 | Nace | ................ | 602/16 |
| 2014/0276250 A1* | 9/2014 | Branch | ................ | 601/5 |

* cited by examiner

*Primary Examiner* — Kim M Lewis
(74) *Attorney, Agent, or Firm* — Larson & Larson, P.A.; Justin P. Miller; Patrick A. Reid (57) ABSTRACT

A double upright knee brace for treating knee flexion contracture includes upper and lower sections, each section having a pair of leg members and an anteriorly disposed integral thigh and shin cuff. A pair of hinges is intermediately positioned to the upper and lower sections. Notches formed in the upper and lower sections provide a catch for a pair of elastic bands, one each deployed on opposed sides of the knee brace, which provide a gait swing assist mechanism for the brace. A multitude of adjustable straps are deployed on both the anterior and posterior sides of the brace. A pair of air bladders, one deployed posteriorly below the knee and one deployed anteriorly above the knee, provide posterior-anterior mobilization when a patient wears the brace, stands up and ambulates. A pair of inner air bladders mounted on inner surfaces of the hinges stabilizes the knee joint.

20 Claims, 5 Drawing Sheets

ORTHOTIC DEVICE FOR TREATING KNEE FLEXION CONTRACTURE

FIELD OF THE INVENTION

This invention relates to orthotic devices in the treatment of joint flexion contractures. In particular, it relates to a knee brace for the treatment of knee joint flexion contracture wherein the knee brace employs air bladders employed at specific locations such that the knee brace can be used while the patient is standing upright and ambulating to provide posterior-anterior mobilization.

BACKGROUND OF THE INVENTION

Orthotic devices and appliances are well known in the prior art for treating a multitude of inflictions in the joints of human patients. The typical joints treated are the wrists, elbows, shoulders, hips, ankles and knees. All types of inflictions can be treated with various known orthotic devices in all of these critical joints. The inflictions include traumatic injury by blunt force, arthritis, abnormal contracture due to stroke, infections in the bones and surrounding tissue, deterioration through old age, excessive use and a myriad of other known medical conditions. All of these inflictions have things in common. They all result in moderate to severe pain in the stricken joint and the inability for the joint to flex and extend without proper treatment and medical intervention. And even in the case of treatment, of which is currently used in the prior art, it still does not return the patient to anywhere near a normal life. Further, the lack of proper flexion and extension inevitably leads to a bevy of secondary problems, such as loss of muscle strength surrounding the stricken joint and lack of use of the stricken joint. In the case of the hips, ankles and knees, many times the patient cannot walk. Or, if the ability to walk still exists, it is done with an improper gait, many times with the use of walker and usually with excruciating pain, which is then typically treated with strong and addictive pain medication therapy.

Nowhere are these problems more prevalent than with the knee joint, and in particular the inability for the leg with the inflicted knee joint to properly extend after it has contracted ("a flexion deformity") due to whatever infliction has been experienced by the patient. This is known has "knee flexion contracture" or the inability for the patient to fully straighten or extend the knee. Normal active range of motion of the knee for a healthy person is 0° extension and 140° flexion. Patients having a flexion deformity, either one or both of them (extension and flexion) are reduced, sometimes severally. Normally, this occurs as a result of failure of knee flexors to lengthen in tandem with the bone, especially when there is inadequate physical therapy to provide active and passive mobilization of the inflicted knee joint.

Prior art devices and methods of treatment (i.e., physical therapy), best used in tandem, do exist to treat knee flexion contracture, but such devices and methods are typically used while the patient lies on bed or sits in a chair. The devices typically employ casting of the knee to employ a custom made brace to affect stretching of the knee flexors. Pressure is applied, just as is done in physical therapy ("PT") when the brace is not employed, by utilizing strapping to affect posterior-anterior mobilization. Or in other words, pressure is applied on top of the thigh (anterior) downward and upon the back of the calf (posterior) upward with strapping while attempting to flex the knee and straighten the leg. These same exercises can be done when not employing the brace by the hands of a physical therapist. However, as stated above, both the known knee braces and the PT are done while the patient lies in bed or sits in a chair. Nowhere in the prior art does a knee brace or other orthotic device exist, which permits the patient to apply posterior-anterior mobilization while the patient stands up, let along while he ambulates.

Accordingly, an improved knee brace is clearly needed to affect posterior-anterior mobilization, which does not regulate the patient to a bed or chair during treatment. Such improved knee brace could be used with continued PT, but would not necessarily be required since the improved knee brace would imitate the PT while the patient ambulates.

Such an improved knee brace would have increased benefits since if the patient is ambulating, then he is also strengthening his muscles above, around and below the knee joint, something that is thought impossible to achieve while employing known flexion contracture knee braces in conjunction with physical therapy.

SUMMARY OF THE INVENTION

We have invented an improved knee brace for treating knee flexion contractures, which overcomes all of the deficiencies seen in the prior art. Our improved knee brace not only stabilizes an inflicted knee joint, which can not fully extend, but it also provides for posterior-anterior mobilization and permits the patient to wear the brace while he ambulates, thereby permitting him to strengthen his muscles above, around and below the knee joint all the while treating his flexion contracture. And the use of such improved knee brace increases the recovering time of persons inflicted with knee flexion contracture over those devices and methods of treatment known in the prior art.

Our knee brace employs a double upright design wherein distinct upper and lower sections are separately attached by a pair of polycentric hinges at lower and upper ends, respectively, of the upper and lower sections. The upper and lower sections each have an integrally formed anteriorly disposed thigh and shin cuff portion, respectively. A multitude of anteriorly and posteriorly disposed adjustable and quick release strapping is employed along the upper and lower sections. A pair of adjustable air bladders is releasably attached along inner surfaces of the hinges. At least one elastic band, on each side of the knee brace, is attached at opposed ends to the lower and upper ends of the upper and lower sections and is align within a groove formed in outer side edges of the hinges for providing a gait swing assist mechanism. The hinges have a multitude of holes formed therein for providing varying degrees and/or ranges of flexion and extension by the use of adjustable stop members.

An anteriorly disposed elongated adjustable air bladder is positioned along inner surfaces of upper section anterior strapping and a posteriorly disposed elongated adjustable air bladder is positioned along inner surfaces of lower section posterior strapping for providing posterior-anterior mobilization when a patient employs the knee brace, stands up and ambulates.

Based upon the unique design of the knee brace briefly summarized directly above, our knee brace allows the patient to wear it as he ambulates and adjust the amount of pressure of each air bladder according to need. He can therefore treat knee flexion contracture as he simultaneously strengthens his surrounding muscles and all the while ambulating and correcting his gait with a goal of achieving proper heel to toe placement during ambulation.

It is therefore a first aspect of the present to provide an orthotic device for treating joint flexion contracture.

It is a second aspect of the present invention to provide a knee brace for treating knee flexion contracture.

It is third aspect of the present invention to provide a double upright knee brace having upper and lower sections separately attached by a pair of hinges.

It is a fourth aspect of the present invention to provide a gait swing assist mechanism attached along the hinges of the knee brace to assist in ambulation and the extension of the leg and knee joint after flexion.

It is a fifth aspect of the present invention to provide for posterior-anterior mobilization while the patient ambulates through the use of air bladders positioned upon the thigh above the knee and behind the calf below the knee.

Many more advantages over the prior art will be evident after considering the Brief Description of the Drawings and the Detailed Description of the Preferred Embodiment set forth herein directly below.

BRIEF DESCRIPTION OF THE DRAWINGS

The detailed description of the invention, contained herein below, may be better understood when accompanied by a brief description of the drawings, wherein.

DETAILED DESCRIPTION OF THE PREFERRED EMBODIMENT

Throughout the following detailed description, the same reference numerals refer to the same elements in all figures.

Figure 1:
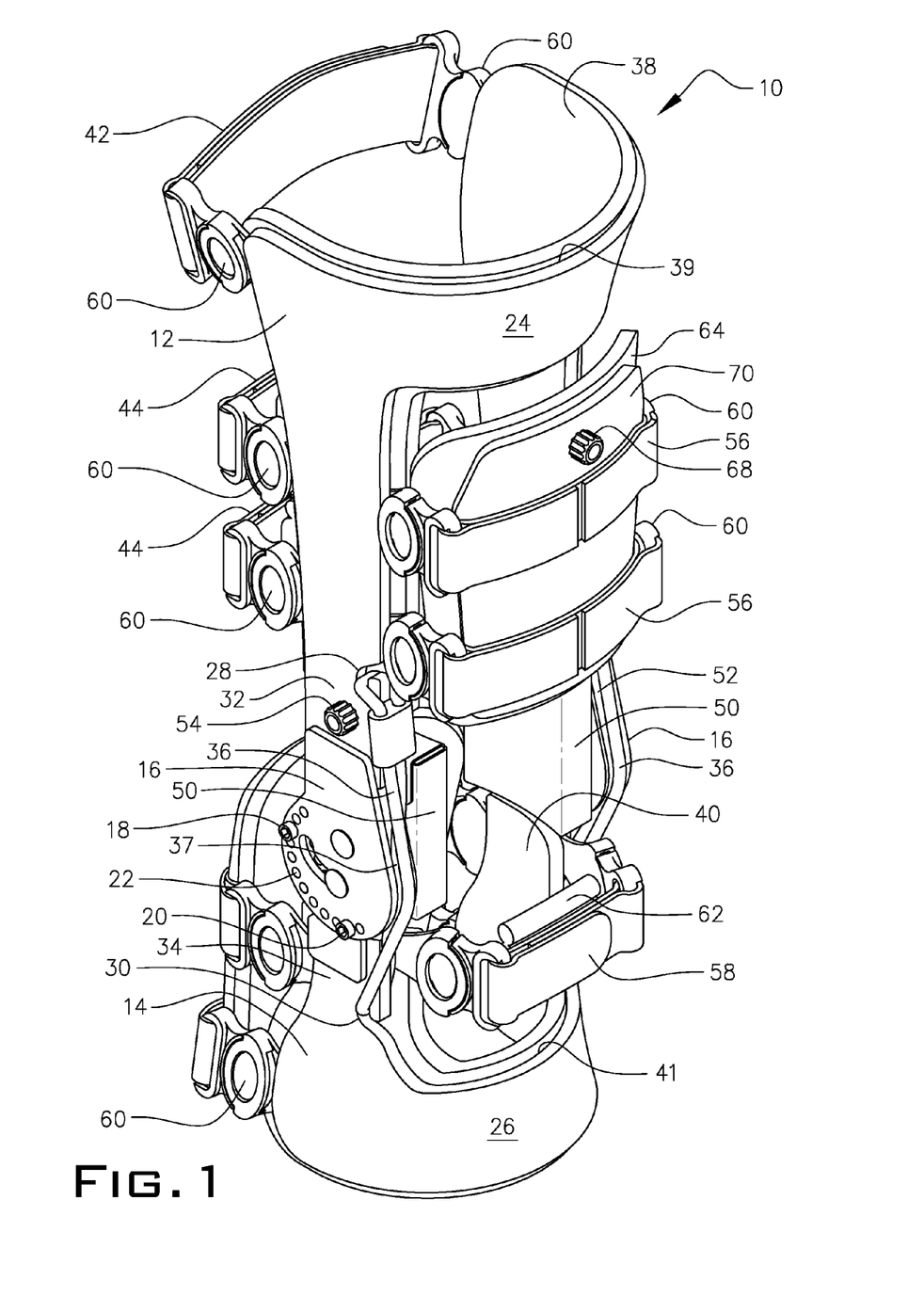
FIG. 1 is a front perspective view of the orthotic device of the present invention in a non-flexed (relaxed) position.
Figure 2:
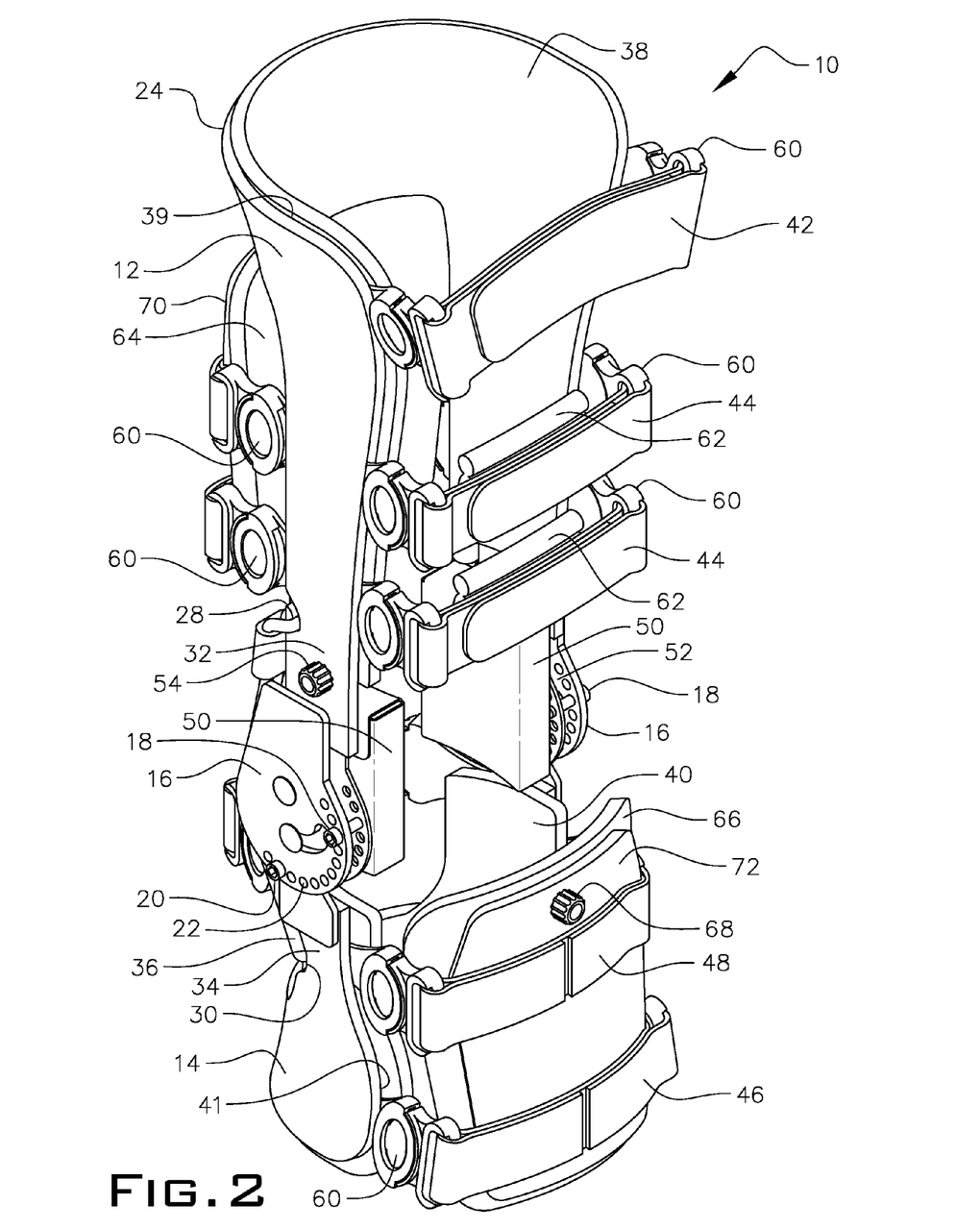
FIG. 2 is a rear perspective view of the orthotic device of the present invention in a non-flexed (relaxed) position.

Referring to FIGS. 1 and 2, an orthotic device for treating knee flexion contractures (also known as a "knee brace") 10 is shown. Knee brace 10 has upper and lower double upright sections, 12 and 14, respectively. Separating upper and lower sections 12 and 14 are a pair of hinges 16. Although unicentric hinges 16 can be employed with knee brace 10 of the present invention, in the preferred embodiment, polycentric hinges are used as shown in FIGS. 1 and 2.

With continuing reference to FIGS. 1 and 2, each hinge 16 has a series of holes 22 formed there through which are used to control, set and/or limit a range of motion of a patient's knee when knee brace 10 is employed on a patient. To set the range of motion, upper and lower adjustable stop members, 18 and 20 respectively, are used in the series of holes 22.

With reference now to just FIG. 1, knee brace upper section 12 has an anterior thigh cuff 24 intermediately positioned the double uprights of upper section 12. Anterior thigh cuff 24 can be attached to the upper section 12 double uprights by any known attachment mechanism. However, in the preferred embodiment, thigh cuff 24 is integrally formed with upper section 12 such that upper section 12 and thigh cuff 24 are one continuous piece of dynamically conformable plastic. Likewise, knee brace lower section 14 has an anterior shin cuff 26 intermediately positioned the double uprights of lower section 12. Anterior shin thigh cuff 26 can also be attached to the lower section 12 double uprights by any known attachment mechanism. However again, in the preferred embodiment, shin cuff 26 is integrally formed with lower section 14 such that lower section 12 and shin cuff 26 are one continuous piece of dynamically conformable plastic.

With reference to both FIGS. 1 and 2, upper section 12 has a pair of upwardly extending notches 28 formed in a lower end 32 of each double upright of upper section 12 on opposed sides of knee brace 10. Likewise, lower section 14 has a pair of downwardly extending notches 30 formed in an upper end 34 of each double upright of lower section on opposed sides of knee brace 10. One or more elastic bands 36 are attached to upwardly extending notches 28 and downwardly extending notches 30 in upper and lower sections, 12 and 14 respectively, at opposed ends of elastic band or bands 36. As shown FIGS. 1 and 2, only one elastic band 36 is employed. However, more than one, preferably two elastic bands 36, can be deployed to provide more resistance and gait swing assist to knee brace 10 when a patient using knee brace 10 flex his or her knee and/or ambulates. Elastic band or bands 36 lay within grooves 37 formed along an outer circumferential edge of each hinge 16.

Still referring to both FIGS. 1 and 2, an inner pad 38 is removeably attached to an inner surface 39 of upper section 12. Likewise, an inner pad 40 is removeably attached to an inner surface 41 of lower section 14. Both inner pads 38 and 40 are used to provide a more comfortable fit to the patient and also work to prevent brace migration when the patient using knee brace 10 ambulates. In a preferred embodiment, hook and loop material is employed. However, other known materials and/or devices can be employed to make inner pads 38 and 40 removeably attachable.

With reference to FIG. 2, a posteriorly positioned upper thigh strap 42 attaches at opposed ends to back edges of upper section 12 where the double uprights meet the rear of the thigh cuff 24. Posteriorly positioned upper thigh strap 42 in conjunction with anteriorly positioned thigh cuff 24, provide a complete circular attachment around the entire circumference of a patient's thigh when knee brace 10 is employed on the leg of the patient. Still further, a pair of posteriorly positioned middle thigh straps 44, positioned below posteriorly positioned upper thigh strap 42, attach at opposed ends to a lateral back edge of the double uprights of upper section 12. Straps 42 and 44 all deploy a quick release snap mechanism 60, which permit straps 42 and 44 to be easily removed and reattached without any special technical skill. Still further, straps 42 and 44 all employ hook and loop material which provides for easy adjustability. Finally, as to straps 44, although not required, in the preferred embodiment, each are provided with removeably attachable comfort pad 62 made of a soft and pliable material that is pleasing to the touch of human skin. Comfort pads 60 also assist in preventing brace migration when knee brace 10 is employed on a patient's leg.

With continuing reference to FIG. 2, a posteriorly positioned lower calf strap 46 attaches at opposed ends to back edges of lower section 14 where the double uprights meet the rear of the shin cuff 26. A posteriorly positioned middle calf strap 48 also attaches at opposed ends to back edges of lower section 14 near the upper end 34. Posteriorly positioned lower and middle calf straps, 46 and 48 respectively, in conjunction with anteriorly positioned shin cuff 26, provide a complete circular attachment around the entire circumference of a patient's calf and shin when knee brace 10 is employed on the leg of the patient. Straps 46 and 48 both deploy the quick release snap mechanism 60, which permit straps 46 and 48 to be easily removed and reattached without any special technical skill. Still further, straps 46 and 48 both employ hook and loop material which provides for easy adjustability.

Referring now to FIG. 1, a pair of anteriorly positioned thigh straps 56 attached at opposed ends thereof to front edges of the double uprights of upper section 12, below thigh cuff 24. Straps 56 also deploy quick release snap mechanism 60 at their opposed ends, which permit straps 56 to be easily removed and reattached. An anteriorly positioned middle shin strap 58 attaches, at opposed ends, to a front edge of upper end 34, of lower section 14. Again, quick release snap mechanisms 60 are deployed at both ends of strap 58. Also, a comfort pad 62 is removeably attached to an inner surface of strap 58 and provides the same functions as those comfort pads deployed on straps 44.

Referring to both FIGS. 1 and 2, a pair of air bladders 50 is removeably attached to inner surfaces 52 of hinges 16. In the preferred embodiment, hook and loop material is used to attach air bladders 50 to inner surfaces 52 of hinges 16, although other materials can be employed in alternate embodiments. A pair of inflation/deflation apertures 54 is formed in the lower end 32 of the double uprights of upper section 12 and which is in direct communication with a tube of each air bladder 50. Air bladders 50 are positioned on knee brace 10 such that they can be inflated and deflated to apply the necessary pressure to the outer surfaces of each knee of the patient using knee brace 10. They accordingly stabilize the knee when the knee brace 10 is being used and also assist in preventing brace migration while the patient ambulates.

Referring to FIG. 1, an upper bladder plate 70 removeably attaches to inner surfaces of the pair of anteriorly positioned thigh straps 56. An elongated anteriorly positioned upper air bladder 64 then removeably attaches to an inner surface of upper bladder plate 70. In the preferred embodiment, hook and loop material is again used, although other known materials have like properties can be employed that allow for upper bladder plate 70 and upper air bladder 64 to be easily removed and repositioned.

Referring to FIG. 2, a lower bladder plate 72 removeably attaches to inner surfaces of posteriorly positioned lower and middle calf straps, 46 and 48 respectively. An elongated posteriorly positioned lower air bladder 66 then removeably attaches to an inner surface of lower bladder plate 72. In the preferred embodiment, hook and loop material is again used, although other known materials have like properties can be employed that allow for lower bladder plate 72 and lower air bladder 66 to be easily removed and repositioned.

Referring to both FIGS. 1 and 2, up and outwardly extending inflation/deflation nozzles 68 are provided on both upper and lower air bladders 64 and 66, extending, in a preferred embodiment, through apertures formed in both upper and lower bladder plates, 70 and 72, at a 45 degree angle. The apertures formed in upper and lower plate plates, 70 and 72, are positioned near top middle edges thereof, respectively.

As shown in FIGS. 1 and 2, both upper and lower bladder plates, 70 and 72, have a slight convex shape which assists knee brace 10, along with the pressure being applied by upper and lower air bladders, 64 and 66, to apply the proper posterior-anterior mobilization to the patient while he or she ambulates. Further, the hinge 16 and elastic bands 36 provide the necessary gait swing assistance mechanism to the patient as he or she flexes and then contracts the leg during ambulation. Proper fitting of the knee brace 10 for each patient is realized through adjustment of all the straps, 42, 44, 46, 48, 56 and 58, proper inflation of air bladders 50 located on the inner surfaces of the hinges 16 and the upper and lower air bladders 64 and 66.

Figure 3:
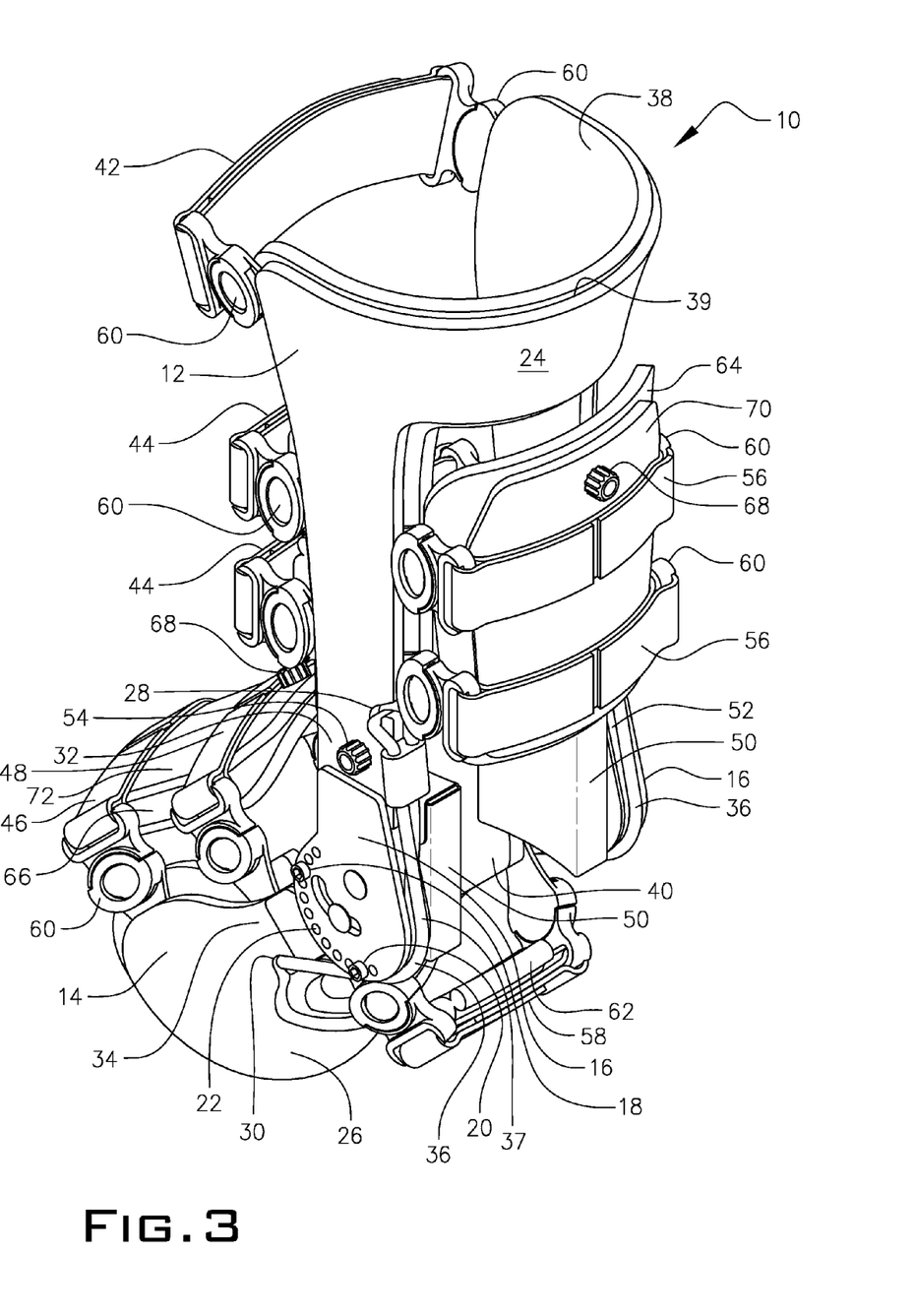
FIG. 3 is a front perspective view of the orthotic device of the present invention in a flexed (tensioned) position.
Figure 4:
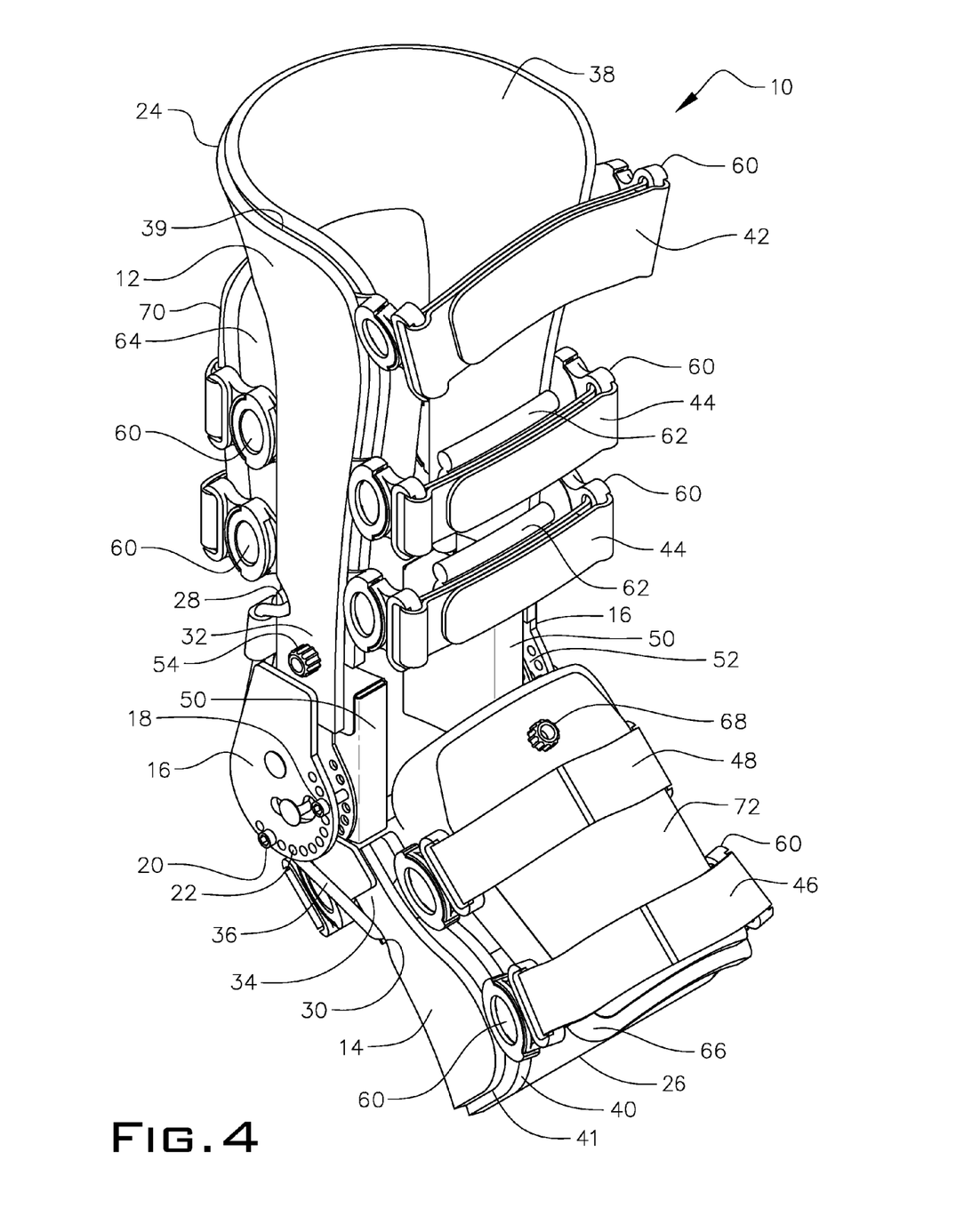
FIG. 4 is a rear perspective view of the orthotic device of the present invention in a flexed (tensioned) position.

Referring to FIGS. 3 and 4, both figures show knee brace 10 in its flexed and tensioned position, whereby FIGS. 1 and 2 show knee brace 10 in its contracted and relaxed position. However, regardless of whether knee brace 10 is in its flexed or contracted position, upper and lower air bladders, 64 and 66, are always applying posterior-anterior mobilization to the patient wearing knee brace 10.

Figure 5:
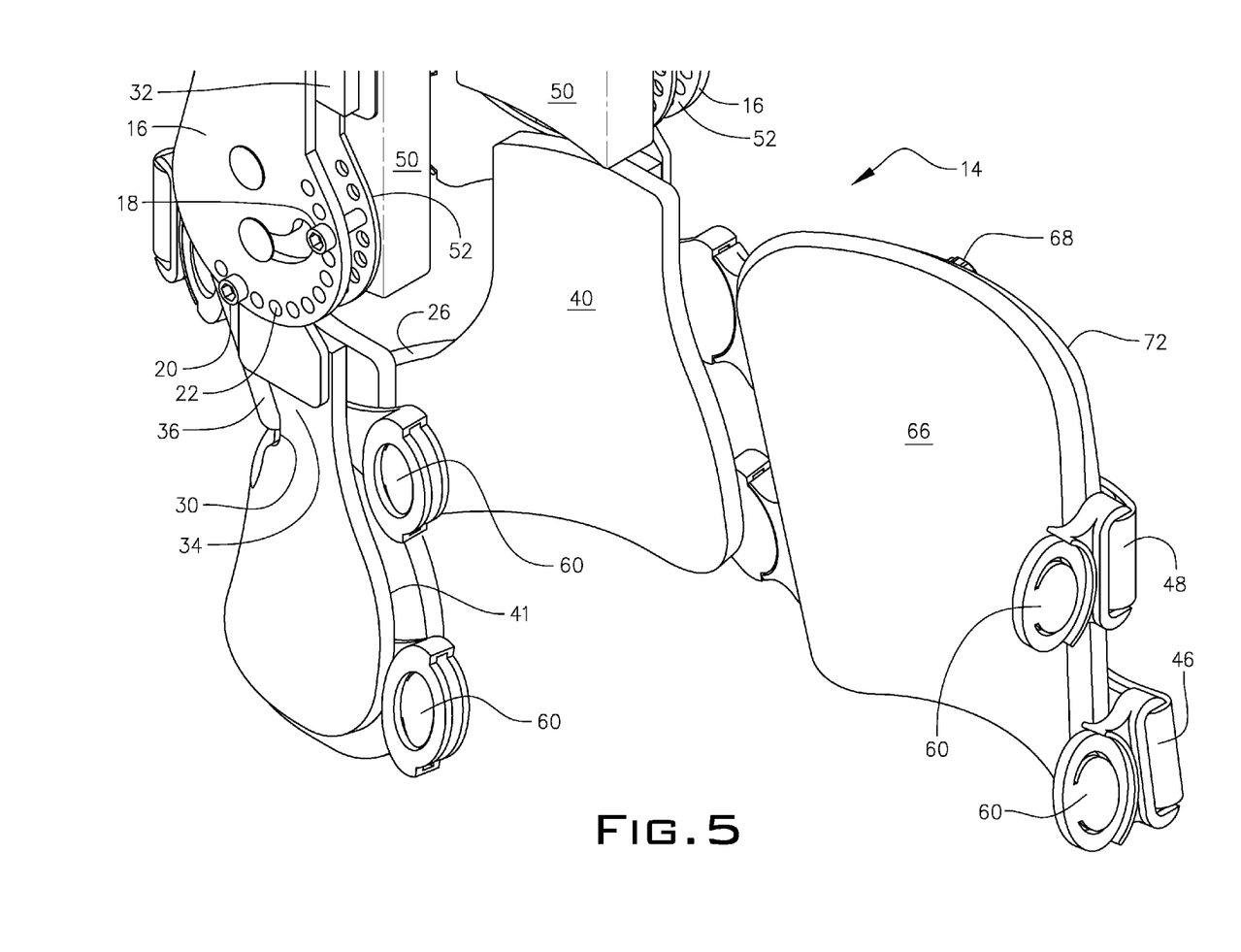
FIG. 5 is a close-up view of the lower section illustrating a quick release mechanism employed on the of multitude of straps of the orthotic device of the present invention when it is in an open or "unsnapped" position and also illustrating how the upper and lower air bladders are attached to the inner surfaces of the upper and lower bladder plates, respectively.

Referring to FIG. 5, lover section 14 is shown and illustrates how straps 46 and 48 can unsnap quickly and easily through the use of quick release snap mechanisms 60. Although all not shown in FIG. 5, all of the straps 42, 44, 46, 48, 56 and 58 are manipulated this way.

Equivalent elements described hereinabove can be substituted for the ones set forth herein to achieve the same results in the same manner and in the same way.

Having thus described invention herein, what is desired to be obtained through Letters Patent is:

1. A double upright knee brace for treating knee flexion contracture, comprising:
   a. upper and lower sections, the upper section having a pair of downwardly extending leg members and an anteriorly disposed thigh cuff positioned between the pair of downwardly extending leg members at an upper end, the lower section having a pair of upwardly extending leg members and an anteriorly disposed shin cuff positioned between the pair of upwardly extending leg members at a lower end;
   b. a pair of rotatable hinges intermediately positioned the upper and lower sections at lower ends of the upper section downwardly extending leg members and upper ends of the lower section upwardly extending leg members, each hinge having a groove formed along a circumferential edge thereof;
   c. a pair of upwardly extending notches formed in the upper section downwardly extending leg members and a reciprocal pair of downwardly extending notches formed in the lower section upwardly extending leg member;
   d. at least two elastic bands, one each deployed on opposed sides of the knee brace, each elastic band attaching to the pairs of notches formed in the upper section downwardly extending leg members and the lower section upwardly extending leg members at opposed ends thereof, the at least two elastic bands lying within the grooves formed along the circumferential edges of hinges, the at least two elastic bands, the pairs of notches and the hinges all forming a gait swing assist mechanism of the knee brace;
   e. at least one anteriorly positioned adjustable elastic strap attached to the upper section downwardly extending leg members at opposed ends thereof;
   f. at least one posteriorly positioned adjustable elastic strap attached to the lower section upwardly extending leg members at opposed ends thereof;
   g. an anteriorly positioned adjustable air bladder removeably attached along an inner surface of the at least one anteriorly positioned elastic strap attached to the upper section downwardly extending leg members for providing anterior mobilization to a thigh of a patient employing the knee brace; and
   h. a posteriorly positioned adjustable air bladder removeably attached along an inner surface of the at least one posteriorly positioned elastic strap attached to the lower section upwardly leg members for providing posterior mobilization to a calf of the patient employing the knee brace.

2. The double upright knee brace of claim 1, further comprising a pair of laterally disposed adjustable air bladders removeably attached along inner side surfaces of the pair of rotatable hinges such that when the knee brace is employed on the patient the pair of laterally disposed adjustable air bladders come in contact with opposed outside surfaces of a knee of the patient.

3. The double upright knee brace of claim 1, further comprising:
   a. a first integral pad member removeably attached along an inner surface of the upper section; and
   b. a second integral pad member removeably attached along an inner surface of the lower section.

4. The double upright knee brace of claim 1, further comprising:
   a. at least one anteriorly positioned adjustable elastic strap attached to the lower section upwardly extending leg members at opposed ends thereof; and
   b. at least one posteriorly positioned adjustable elastic strap attached to the upper section downwardly extending leg members at opposed ends thereof.

5. The double upright knee brace of claim 4, further comprising:
   a. an at least one first horizontally disposed removeably attachable pad attached to an inner surface of the at least one anteriorly positioned adjustable elastic strap attached to the lower section upwardly extending leg members; and
   b. an at least one second horizontally disposed removeably attachable pad attached to an inner surface of the at least one posteriorly positioned adjustable elastic strap attached to the upper section downwardly extending leg members.

6. The double upright knee brace of claim 1, wherein the thigh cuff is integrally formed with the upper section downwardly extending leg members and the shin cuff is integrally formed with the lower section upwardly extending leg members.

7. The double upright knee brace of claim 1, wherein the pair of rotatable hinges are polycentric hinges.

8. The double upright knee brace of claim 7, where each polycentric hinge includes a plurality of holes formed therein for providing a controllable range of knee flexion and extension motion, each hinge further including a pair of adjustable stop member pins for positioning in the plurality of holes to set a desired controllable range of knee flexion and extension motion.

9. The double upright knee brace of claim 1, wherein all of the straps employ quick release mechanisms at their respective opposing ends.

10. The double upright knee brace of claim 1, wherein the at least one anteriorly positioned adjustable elastic strap attached to the upper section downwardly extending leg members at opposed ends thereof comprises two straps.

11. The double upright knee brace of claim 10, further comprising an upper bladder plate removeably attached to inner surfaces of the two anteriorly positioned adjustable elastic straps and intermediately disposed the anteriorly positioned adjustable air bladder and the two anteriorly positioned adjustable elastic straps.

12. The double upright knee brace of claim 1, wherein the at least one posteriorly positioned adjustable elastic strap attached to the lower section upwardly extending leg members at opposed ends thereof comprises two straps.

13. The double upright knee brace of claim 1, further comprising a lower bladder plate removeably attached to inner surfaces of the two posteriorly positioned adjustable elastic straps and intermediately disposed the posteriorly positioned adjustable air bladder and the two posteriorly positioned adjustable elastic straps.

14. A double upright knee brace for treating knee flexion contracture, comprising:
   a. upper and lower sections, the upper section having a pair of downwardly extending leg members and an anteriorly disposed thigh cuff integrally positioned between the pair of downwardly extending leg members at an upper end, the lower section having a pair of upwardly extending leg members and an anteriorly disposed shin cuff integrally positioned between the pair of upwardly extending leg members at a lower end;
   b. a pair of rotatable polycentric hinges intermediately positioned the upper and lower sections, each hinge having a groove formed along a circumferential edge thereof;
   c. a pair of upwardly extending notches formed in the upper section downwardly extending leg members and a reciprocal pair of downwardly extending notches formed in the lower section upwardly extending leg member;
   d. at least two elastic bands, one each deployed on opposed sides of the knee brace, each elastic band attaching to the pairs of notches formed in the upper section downwardly extending leg members and the lower section upwardly extending leg members at opposed ends thereof, the at least two elastic bands lying within the grooves formed along the circumferential edges of hinges, the at least two elastic bands, the pairs of notches and the hinges all forming a gait swing assist mechanism of the knee brace;
   e. a pair of anteriorly positioned adjustable elastic straps attached to the upper section downwardly extending leg members at opposed ends thereof;
   f. a pair of posteriorly positioned adjustable elastic straps attached to the lower section upwardly extending leg members at opposed ends thereof;
   g. an upper elongated plate member removeably attached to the pair of upper section anteriorly positioned adjustable elastic straps along inner surfaces thereof and a lower elongated plate member removeably attached to the pair of lower section posteriorly positioned adjustable elastic straps along inner surfaces thereof; and
   h. an anteriorly positioned adjustable air bladder removeably attached to an inner surface of the upper elongated plate member and a posteriorly positioned adjustable air bladder removeably attached along an inner surface of lower elongated plate member.

15. The double upright knee brace of claim 14, further comprising a pair of laterally disposed adjustable air bladders removeably attached along inner side surfaces of the pair of rotatable polycentric hinges such that when the knee brace is employed on the patient the pair of laterally disposed adjustable air bladders come in contact with opposed outside surfaces of a knee of the patient.

16. The double upright knee brace of claim 14, further comprising:
   a. a first integral pad member removeably attached along an inner surface of the upper section; and
   b. a second integral pad member removeably attached along an inner surface of the lower section.

17. The double upright knee brace of claim 14, further comprising:
   a. one anteriorly positioned adjustable elastic strap attached to the lower section upwardly extending leg members at opposed ends thereof; and b. three posteriorly positioned adjustable elastic straps attached to the upper section downwardly extending leg members at opposed ends thereof.

18. The double upright knee brace of claim 17, further comprising at least one horizontally disposed removeably attachable pad attached to an inner surface of one or more of the anteriorly and posteriorly adjustable straps of which are not attached to the upper and lower elongated plate members.

19. The double upright knee brace of claim 14, wherein each polycentric hinge includes a plurality of holes formed therein for providing a controllable range of knee flexion and extension motion, each hinge further including a pair of adjustable stop member pins for positioning in the plurality of holes to set a desired controllable range of knee flexion and extension motion.

20. The double upright knee brace of claim 14, wherein all of the straps employ quick release mechanisms at their respective opposing ends.

\* \* \* \* \*